(12) United States Patent
Hoshino et al.

(10) Patent No.: US 7,687,246 B2
(45) Date of Patent: Mar. 30, 2010

(54) PROCESS FOR PRODUCING CAROTENOIDS

(75) Inventors: Tatsuo Hoshino, Kamakura (JP);
Setsuko Masuda, Yokohama (JP);
Yutaka Setoguchi, Fujisawa (JP)

(73) Assignee: DSM IP Assets B. V., TE Heerlen (NL)

( * ) Notice: Subject to any disclaimer, the term of this patent is extended or adjusted under 35 U.S.C. 154(b) by 539 days.

(21) Appl. No.: 10/518,530

(22) PCT Filed: Apr. 10, 2003

(86) PCT No.: PCT/EP03/03742

§ 371 (c)(1),
(2), (4) Date: Jun. 20, 2005

(87) PCT Pub. No.: WO04/001057

PCT Pub. Date: Dec. 31, 2003

(65) Prior Publication Data

US 2005/0260700 A1    Nov. 24, 2005

(30) Foreign Application Priority Data

Jun. 21, 2002    (EP)  .................................. 02013784

(51) Int. Cl.
*C12P 23/00*    (2006.01)
(52) U.S. Cl. ...................... 435/67; 435/244; 435/254.2; 435/911
(58) Field of Classification Search .................. None
See application file for complete search history.

(56) References Cited

U.S. PATENT DOCUMENTS

| | | |
|---|---|---|
| 5,182,208 A | 1/1993 | Johnson et al. |
| 5,356,809 A | 10/1994 | Johnson et al. |
| 5,972,642 A | 10/1999 | Flenø et al. |
| 6,972,191 B2 * | 12/2005 | Muramatsu et al. ......... 435/155 |

FOREIGN PATENT DOCUMENTS

| | | |
|---|---|---|
| JP | 2002 300896 | 10/2002 |
| WO | WO 96/09393 | 3/1996 |
| WO | WO 00/01650 | 1/2000 |

OTHER PUBLICATIONS

Ducrey et al., Yeast, 1998, vol. 14, pp. 1007-1016.*
An et al., Applied and Environmental Microbiology, Jan. 1989, vol. 51,p. 116-124.*
Golubev, W.I. "Perfect State of *Rhodomyces dendrorhous* (Phaffia rhodozyma)," *Yeast*, vol. 11, pp. 101-110 (1995).
Misawa, N. et al. "Elucidation of the *Erwinia uredovora* Carotenoid Biosynthetic Pathway by Functional Analysis of Gene Products Expressed in *Escherichia coli*," *Journal of Bacteriology*, vol. 172, No. 12, pp. 6704-6712 (1990).
Yamano, S. et al. "Metabolic Engineering for Production of β-Carotene and Lycopene in *Saccharomyces cerevisiae*", *Biosci. Biotech. Biochem.*, vol. 58, No. 6, pp. 1112-1114 (1994).
Miura, Y. et al. "Production of Lycopene by the Food Yeast, *Candida utilis* That Does Not Naturally Synthesize Carotenoid", *Biotechnology and Bioengineering*, vol. 58, Nos. 2 & 3, pp. 306-308 (1998).
Johnson, E.A. and An, G. "Astaxanthin from Microbial Sources", *Critical Reviews in Biotechnology*, vol. 11, No. 4, pp. 297-326 (1991).
Biller, S.A. et al., "Squalene Synthase Inhibitors", *Current Pharmaceutical Design*, vol. 2, No. 1, pp. 1-40.
Robinson G.W. et al., "Conservation between Human and Fungal Squalene Synthetases: Similarities in Structure, Function, and Regulation " *Molecular and Cellular Biology*, vol. 13, No. 5, pp. 2706-2717 (1993).
Derwent Database, (Abstract No. XP002250540) English language abstract of JP 2002 300896 (document B3 above).

* cited by examiner

*Primary Examiner*—Irene Marx
(74) *Attorney, Agent, or Firm*—Bryan Cave LLP

(57) ABSTRACT

The present invention relates to a biological process for producing carotenoids utilizing a microorganism which is capable of producing carotenoids and belonging to the genus *Xanthophyllomyces* (*Phaffia*) in the presence of an inhibitor for biosynthesis of sterols from farnesyl pyrophosphate.

3 Claims, No Drawings

PROCESS FOR PRODUCING CAROTENOIDS

This application is the National Stage of International Application No. PCT/EP2003/003742, filed Apr. 10, 2003.

The present invention relates to a biological process for producing carotenoids utilizing a microorganism which is capable of producing carotenoids and belonging to the genus *Xanthophyllomyces* (*Phaffia*) in the presence of an inhibitor for biosynthesis of sterols from farnesyl pyrophosphate (hereinafter referred to as FPP).

Over 600 different carotenoids have been described from carotenogenic organisms found among bacteria, yeast, fungi and plants. Currently only two of them, beta-carotene and astaxanthin are commercially produced in microorganisms and used in the food and feed industry. These carotenoids are industrially important as natural pigments and as functional substances for human health with their powerful antioxidant properties. Moreover, from a commercial prospect, there is an increasing demand for astaxanthin as a coloring reagent especially in the fish farming industry, such as salmon farming, because astaxanthin imparts a distinctive orange-red coloration to the fish and contributes to consumer appeal.

Other carotenoids, for example, lycopene, zeaxanthin, canthaxanthin, and beta-cryptoxanthin, are also industrially important as natural pigments and as antioxidants. Lycopene is shown in experiments performed in vitro to quench singlet oxygen efficiently. Lycopene inhibits lipid peroxidation, and serum levels of this carotenoid inversely related to the risk of cancer in the pancreas and cervix. The red color of fruits and vegetables such as tomatoes, pink grapefruit, the skin of red grapes, watermelon and red guavas is due to lycopene. Other dietary sources include papaya and apricots. Zeaxanthin is a yellow-colored carotenoid, which is an oxidized hydroxy derivative of beta-carotene. Zeaxanthin is abundant in spinach and corn and many other plant species. This is a strong antioxidant and found also in the retina. It is widely believed that zeaxanthin acts to filter and shield harmful blue light from the eye and protect against age-related macular degeneration. Canthaxanthin is a red-colored carotenoid, found in many plants and animals. It is used for pigmentation of egg yolk, broiler, and farmed trout, and used in foods and cosmetics requiring a more orange-red color. Canthaxanthin also functions as a singlet oxygen quencher and free radical deactivator. Beta-cryptoxanthin is a yellow-colored carotenoid found in oranges, mango, papaya, squash and many other fruits. Beta-cryptoxanthin is recognized also as a strong antioxidant useful for prevention from cancer.

Among the microorganisms which are capable of producing remarkable amounts of carotenoids, *Phaffia rhodozyma* is one of the most well-known carotenogenic strains. This yeast strain produces astaxanthin and is one of the few microorganisms which are currently used to provide astaxanthin in the food and feed industry. In a recent taxonomic study, a sexual cycle of *Phaffia rhodozyma* was revealed and its telemorphic state was designated under the name of *Xanthophyllomyces dendrorhous* [Golubev, Yeast 11:101-110 (1995)]. In the present description, the widely recognized name, *Phaffia rhodozyma* is used.

Several studies to increase the level of carotenoids production by microorganisms including, for example, construction of recombinant microorganisms which were genetically engineered to obtain the ability to produce a remarkable amount of several carotenoids using appropriate host strains such as *Escherichia coli*, *Saccharomyces cerevisiae*, or *Candida utilis* [Misawa et al., J. Bacteriol. 172:6704 (1990); Yamano et al., Biosci. Biotech. Biochem. 58:1112 (1994); Miura et al., Biotechnol. Bioeng. 58:306 (1998)], strain improvement to obtain hyper-producers, for example, of astaxanthin from *Phaffia rhodozyma* [Johnson et al., Critical Reviews in Biotechnology 11:297-326 (1991)], and process improvement to optimize the fermentation process, for example, for astaxanthin production by *Phaffia rhodozyma* (U.S. Pat. No. 5,972, 642) have been conducted. It was described in U.S. Pat. No. 5,356,809 that addition of antimycin or another inhibitor of the main respiratory chain to *Phaffia rhodozyma* cells enhanced the astaxanthin production. But this is not a much efficient or convenient method. Clearly, there is still a need for a simple and efficient method of increasing the production yields of carotenoids.

One embodiment of the present invention is a biological process for producing carotenoids which comprises cultivating a microorganism which is capable of producing carotenoids in the presence of an inhibitor for biosynthesis of sterols from FPP, in an aqueous nutrient medium under aerobic conditions.

It is more preferable to use highly carotenogenic microorganisms, e.g. those belonging to the genus *Xanthophyllomyces* (*Phaffia*). Thus, a preferable example of the said microorganism of the present invention is a microorganism belonging to the genus *Xanthophyllomyces* (*Phaffia*). A preferable strain of *Xanthophyllomyces* (*Phaffia*) of the present invention can be obtained from the American Type Culture Collection, 10801 University Blvd., Manassas, Va. 20110-2209, U.S.A. as *Xanthophyllomyces* (*Phaffia*) ATCC96594 (redeposited under the accession No. ATCC 74438 on Apr. 8, 1998 pursuant to the Budapest Treaty).

The present invention is thus particularly concerned with a biological process for producing carotenoids which comprises cultivating a microorganism which is capable of producing carotenoids and belonging to the genus *Xanthophyllomyces* (*Phaffia*) in the presence of an inhibitor for biosynthesis of sterols from FPP, and a substrate for producing carotenoids in an aqueous nutrient medium under aerobic conditions, and isolating the resulting carotenoids from the cells of said microorganism or from the cultured broth.

Especially, it will be more preferable, for the said biological process of the present invention, to inhibit the first reaction of the sterol pathway, which is catalysed by squalene synthase.

Squalene synthase (also referred to in the art as squalene synthetase) inhibitors are reported to lower cellular sterol levels. Squalene synthase is an enzyme which catalyses the first committed step of sterol biosynthesis. Two molecules of FPP are condensed to form squalene.

Thus, a further embodiment of the present invention is a biological process for producing carotenoids which comprises cultivating a microorganism which is capable of producing carotenoids in the presence of an inhibitor for squalene synthase.

Several kinds of squalene synthase inhibitors have been reported [Biller et al., Current Pharmaceutical Design 2:1-40 (1996)]. There have been reported roughly three groups of squalene synthase inhibitors, ammonium ion based squalene synthase inhibitors, phosphorus containing FPP mimetics, and carboxylate-based inhibitors. Any kinds of squalene synthase inhibitors are preferable for the present invention. One of the preferable examples of such squalene synthase inhibitors is an ammonium ion based squalene synthase inhibitor.

Further, one of the preferable examples of the ammonium ion based squalene synthase inhibitor is a phenoxypropylamine-type squalene synthase inhitor [Brown et al, Journal of Medicinal Chemistry 38:4157-4160 (1995)]. A large number of phenoxypropylamine-type squalene synthase inhitors including, for example, [3-(3-allyl-biphenyl-4-yloxy)propyl]-isopropyl-amine, N-isopropyl-3-(4-acetamido-2-allylphenoxy) propylamine, N-methyl-N-isopropyl-3-(4-acetamide-2-allylphenoxy) propylamine, N-cyclopentyl-3-(4-acetamido-2-allylphenoxy) propylamine, N-cyclobutyl-3-(4-acetamide-2-allylphenoxy) propylamine, N-isopropyl-3-(2-allyl-4-butyramidophenoxy) propylamine, N-isopropyl-3-(4-acetamido-2-chlorophenoxy) propylamine, N-isopropyl-3-(4-acetamido-2-propylphenoxy) propylamine, and N-isopropyl-3-(4-acetamido-2-allylphenoxy)-1-methylpropylamine, or biologically acceptable salt thereof, have been known (Brown et al., supra).

The preferable squalene synthase inhibitor used in the present Examples is [3-(3-allyl-bi-phenyl-4-yloxy)-propyl]-isopropyl-amine, N-isopropyl-3-(4-acetamido-2-allylphenoxy) propylamine and N-methyl-N-isopropyl-3-(4-acetamide-2-allylphenoxy) propylamine.

Carotenoids are normally produced by cultivating a carotenogenic microorganism in a medium which comprises suitable macro- and micronutrients for the cells, such as molasses, saccharose or glucose as a carbohydrate source for cell growth and also as a substrate for producing carotenoids, and nitrogen sources such as corn steep liquor, yeast extract, diammonium sulphate, ammonium phosphate, ammonium hydroxide or urea, phosphorus sources such as ammonium phosphate and phosphoric acid and added micronutrients or mineral salts such as magnesium sulphate, zinc sulphate and biotin or desthiobiotin.

The preferable conditions for cultivation are a pH range from 4 to 8 and a temperature range from 15 to 26° C. for 24 to 500 hours. The more preferable conditions for cultivation are a pH range from 5 to 7 and a temperature range from 18 to 22° C. for 48 to 350 hours.

In the cultivation, aeration and agitation usually give favorable results for the production of carotenoids.

In the present invention, the inhibitor for sterol biosynthesis from FPP is added to the medium. Suitably, the concentration of the inhibitor is varied based on the species of inhibitor and microorganism used for the carotenoids production, e.g. in a range of concentration that gives less than 50% reduction of the cell growth in the carotenoids producing conditions. A more preferable concentration of the inhibitor may be in the range of concentration that gives less than 30% reduction of the cell growth.

In the present invention, the inhibitor for sterol biosynthesis from FPP can be added to the medium at any period of the cultivation.

Carotenoids produced by cultivating a carotenogenic microorganism using the methods of the present invention, can be isolated either from the medium, in the case they are secreted into the medium, or from the cells of the microorganism and, if necessary separated from other carotenoids that may be present in case one specific carotenoid is desired, by methods known in the art [e.g., Carotenoids Vol IA: Isolation and Analysis, Britton et al., Birkhauser Verlag, Basel (1995)].

Carotenoids produced in accordance with the present invention can be used in a process for the preparation of food or feeds. A man skilled in the art is familiar with such processes. Such compound foods or feeds can further comprise additives or components generally used for such purpose and known in the state of the art.

The following Examples further illustrate the present invention, but these are not thereby limiting the scope of the invention.

The squalene synthase inhibitor used in the Examples is [3-(3-allyl-biphenyl-4-yloxy)propyl]-isopropyl-amine, one of the series of phenoxypropylamine-type inhibitors. This compound was synthesized according to methods described by Brown et al. (supra): 3-Allyl-biphenyl-4-ol was prepared from biphenyl-4-ol (product code H7751, Sigma, USA) by reaction with allyl bromide and potassium carbonate in butan-2-one, and thermal rearrangement. 3-Allyl-biphenyl-4-ol was reacted with 1,3-dibromopropane and potassium carbonate in butan-2-one, and subsequent reaction with isopropylamine in 2-propanol gave [3-(3-allyl-biphenyl-4-yloxy)-propyl]-isopropyl-amine.

EXAMPLE 1

Effect of Addition of the Squalene Synthase Inhibitor on the Cell Growth of *Phaffia rhodozyma*

*Phaffia rhodozyma* ATCC96594 (redeposited under the accession No. ATCC 74438 on Apr. 8, 1998 pursuant to the Budapest Treaty) was inoculated into YPD medium (DIFCO, Detroit, U.S.A., 10 mL in tube) and cultivated by shaking at 20° C. for 2 days. 0.5 mL of the culture was inoculated into fresh YPD medium (10 mL in tube) containing 30 g/L of glucose and 0, 0.2, 0.5, 1.0, 2.0, 5.0, 10.0, and 20.0, μg/mL, respectively, of [3-(3-allyl-biphenyl-4-yl-oxy)-propyl]-isopropyl-amine, and cultivated by shaking at 20° C. for 5 days.

An aliquot of the culture was withdrawn occasionally during the cultivation, and optical density at 660 nm was measured by using UV-1200 photometer (Shimadzu Corp., Kyoto, Japan) for analysis of the cell growth. The results are shown in Table 1.

TABLE 1

| [3-(3-allyl-biphenyl-4-yloxy)-propyl]-isopropyl-amine | Cell growth (OD at 660 nm) | | | |
|---|---|---|---|---|
| [μg/mL] | Day 1 | Day 2 | Day 3 | Day 5 |
| 0 | 4.4 | 15.9 | 20.1 | 19.0 |
| 0.2 | 4.5 | 16.7 | 20.1 | 19.3 |
| 0.5 | 4.4 | 15.6 | 20.4 | 19.4 |
| 1.0 | 4.0 | 15.0 | 20.0 | 19.5 |
| 2.0 | 3.6 | 15.0 | 19.5 | 19.0 |
| 5.0 | 2.9 | 12.3 | 18.8 | 18.0 |
| 10.0 | 2.0 | 5.6 | 14.7 | 16.9 |
| 20.0 | 1.2 | 1.7 | 2.7 | 7.0 |

The cell growth was not affected when the concentration of the squalene synthase inhibitor was not higher than 2.0 μg/mL. About 23% inhibition of the cell growth was observed at Day 2 by 5.0 μg/mL of the inhibitor.

EXAMPLE 2

Effect of Addition of the Squalene Synthase Inhibitor on the Astaxanthin Production by *Phaffia rhodozyma*

*Phaffia rhodozyma* ATCC96594 (redeposited under the accession No. ATCC 74438 on Apr. 8, 1998 pursuant to the Budapest Treaty) was inoculated into YPD medium as in Example 1 and cultivated by shaking at 20° C. for 2 days. 2.5 ml of the culture were inoculated into fresh YPD medium (50 mL in flask) containing 22 g/L of glucose and 0, 0.5, 1.0, 2.0, and 5.0, μg/mL, respectively, of [3-(3-allyl-biphenyl-4-yloxy)-propyl]-isopropyl-amine, and cultivated by shaking at 20° C. for 7 days. On Day 2 of the cultivation, 50 g/L of glucose was added to the culture. Addition of the inhibitor in the middle of the cultivation was also tested. An aliquot of the culture was withdrawn at Day 4 and Day 7 of the cultivation, and optical density at 660 nm (by using the same method described in Example 1) and astaxanthin content in the culture were measured.

For analysis of the content of astaxanthin, the withdrawn broth was mixed with a solvent mixture (ethyl alcohol, hexane and ethyl acetate) and carotenoids were extracted from the cells of *Phaffia rhodozyma* by vigorous shaking with glass beads. After extraction, disrupted cells and glass beads were removed by centrifugation and the resultant supernatant was analyzed by HPLC for the astaxanthin content. The HPLC conditions used were as follows:

| | |
|---|---|
| HPLC column: | Chrompack Lichrosorb si-60 (4.6 mm, 250 mm) |
| Temperature: | room temperature |
| Eluent: | acetone/hexane (18/82) add 1 ml/L of water to eluent |
| Injection volume: | 10 µl |
| Flow rate: | 2.0 ml/minute |
| Detection: | UV at 450 nm |

A reference sample of astaxanthin was obtained from Hoffmann La-Roche (Basel, Switzerland). The results are shown in Table 2.

TABLE 2

| [3-(3-allyl-biphenyl-4-yloxy)-propyl]-isopropyl-amine | Astaxanthin content* (relative values) | | Cell growth (OD at 660 nm) | |
|---|---|---|---|---|
| [µg/mL] | Day 4 | Day 7 | Day 4 | Day 7 |
| 0 | 69 | 100 | 40.7 | 40.0 |
| 0.5 | 75 | 114 | 39.6 | 39.8 |
| 1.0 | 77 | 118 | 40.3 | 39.8 |
| 2.0 | 75 | 125 | 38.2 | 39.3 |
| 5.0 | 67 | 129 | 40.2 | 39.5 |
| 5.0** | 84 | 131 | 37.4 | 37.9 |

*Relative values calculated as the astaxanthin content of Day 7 without inhibitor to be 100.
**Cultivation was started without inhibitor, and 5.0 µg/mL of inhibitor was added at Day 2 of the cultivation.

Astaxanthin production was enhanced in all conditions tested. The best result was obtained when the inhibitor was added at Day 2 of the cultivation, but addition of the inhibitor from the beginning of the cultivation was also effective on the astaxanthin production.

The invention claimed is:

1. A biological process for producing carotenoids including astaxanthin, the process comprising cultivating a microorganism which is *Xanthophyllomyces dendrorhous* (*Phaffia rhodozyma*) ATCC96594, redeposited under accession No. ATCC 74438, in the presence of [3-(3-allyl-biphenyl-4-yloxy)-propyl]-isopropyl-amine, a substrate for producing carotenoids which include astaxanthin, in an aqueous nutrient medium under aerobic conditions wherein the concentration of the inhibitor in the aqueous medium is from 0.5 µg/ml to 5.0 µg/ml, and isolating the resulting carotenoids which include astaxanthin, from the cells of said microorganism or from the cultured medium.

2. The process according to claim 1, wherein the cultivation is carried out at a pH in the range from 4 to 8 and at a temperature in the range from 15 to 26° C., for 24 to 500 hours.

3. The process according to claim 2, wherein the cultivation is carried out at a pH in the range from 5 to 7 and at a temperature in the range from 18 to 22° C., for 48 to 350 hours.

* * * * *